United States Patent
Al-Ghamdi et al.

(10) Patent No.: US 12,007,369 B2
(45) Date of Patent: Jun. 11, 2024

(54) RESIDUAL CORROSION INHIBITOR MONITORING

(71) Applicant: Saudi Arabian Oil Company, Dhahran (SA)

(72) Inventors: Talal M. Al-Ghamdi, Dhahran (SA); Muhaned M. Feghia, Khobar (SA); Faisal M. Mutahhar, Dhahran (SA); Musab M. Talal, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 160 days.

(21) Appl. No.: 17/220,505

(22) Filed: Apr. 1, 2021

(65) Prior Publication Data

US 2022/0317096 A1 Oct. 6, 2022

(51) Int. Cl.
*G01N 30/06* (2006.01)
*G01N 30/12* (2006.01)

(52) U.S. Cl.
CPC ....... *G01N 30/06* (2013.01); *G01N 2030/062* (2013.01); *G01N 2030/065* (2013.01); *G01N 2030/121* (2013.01)

(58) Field of Classification Search
CPC ............. G01N 30/06; G01N 2030/062; G01N 2030/065; G01N 2030/121
See application file for complete search history.

(56) References Cited

U.S. PATENT DOCUMENTS 5,420,151 A * 5/1995 Hammarberg ....... C07D 311/58
549/404
10,197,547 B2 * 2/2019 Cooks ................ G01N 33/2823

FOREIGN PATENT DOCUMENTS

| CA | 2249171 A1 | * 4/1999 | ........... C07C 233/36 |
| CN | 107283567 | * 10/2017 | |
| EP | 38668 | * 10/1981 | |
| KR | 100193590 | 6/1999 | |
| RU | 2563602 | 9/2015 | |
| WO | WO-2011006019 A2 | * 1/2011 | ............. A23K 10/12 |

(Continued)

OTHER PUBLICATIONS https://www.spl-inc.com/wp-content/uploads/2021/12/SPL-113019-CrudeOilAssay_PO.pdf (Year: 2021).*

(Continued)

*Primary Examiner* — John E Breene
*Assistant Examiner* — Alex T Devito
(74) *Attorney, Agent, or Firm* — Fish & Richardson P.C.

(57) ABSTRACT

A method for determining corrosion inhibitor residual concentration of a hydrocarbon sample is described. The hydrocarbon sample is mixed with a standard solution to form a first mixture. The standard solution includes a corrosion inhibitor in a known concentration. The first mixture is mixed with an aqueous saline solution to form a second mixture. The aqueous saline solution includes about 1% salt concentration or greater. The second mixture is agitated for about 1 hour or longer and at a temperature of about 50 degrees Celsius (° C.) or greater. After agitation, a hydrocarbon phase and an aqueous phase of the second mixture are allowed to separate. A portion of the aqueous phase is obtained. The portion of the aqueous phase is analyzed to determine a corrosion inhibitor residual concentration of the hydrocarbon sample.

9 Claims, 6 Drawing Sheets

(56) References Cited

FOREIGN PATENT DOCUMENTS

WO     WO-2014120552 A1 *   8/2014            G01N 30/724

OTHER PUBLICATIONS

Al-Ghamdi et al., "Determination of corrosion inhibitor residuals in inhibited diesel used for mothballing activities," ChemIndex 2016, Saudi Aramco, 2016, 1 page.

Cavallaro et al., "Cost-conscious corrosion control," SPE-179949-MS, presented at the SPE International Oilfield Conference and Exhibition, Aberdeen, Scotland, May 9-10, 2016, 11 pages.

Fortenberry et al., "Analysis of Residual Corrosion Inhibitors in Oilfield Brines" SPE 26607, presented at the 68th Annual Technical Conference and Exhibition of the Society of Petroleum Engineers, Houston, Texas, Oct. 3-6, 1993, 15 pages.

Gough et al., "Molecular Monitoring of Residual Corrosion Inhibitor Actives in Oilfield Fluids: Implications for Inhibitor Performance," Corrosion 98, Paper No. 33, NACE International, 1998, 12 pages.

Kang et al., "Study of sweet corrosion at low water cut in multiphase pipelines," SPE 56465, presented at the 1999 SPE Annual Technical Conference and Exhibition, Houston, Texas, Oct. 3-6, 1991, 8 pages.

Olabisi et al., "The Role of Bacteria Population Density in Wet and Dry Crude Asset Integrity," Corrosion 2015 Conference & Expo, NACE International, Paper 5534, 2015, 17 pages.

Soltani, "Reliable level of corrosion inhibitor's residual concentration in wet gas-condensate pipelines," The European Corrosion Congress, Eurocorr, Sep. 2020, 13 pages.

Son et al., "Analysis of Residual Corrosion Inhibitors by Fluorescence and Ultraviolet Spectrophotometry," Corrosion 1996, Paper # 344, NACE International Annual Conference and Exhibition, 23 pages.

* cited by examiner

RESIDUAL CORROSION INHIBITOR MONITORING

TECHNICAL FIELD

This disclosure relates to monitoring residual corrosion inhibitor content in hydrocarbon-containing fluids.

BACKGROUND

Corrosion can occur in oil and gas processing equipment and piping. Corrosion can occur due to factors such as temperature, the presence of carbon dioxide, the presence of hydrogen sulfide, the presence of electrolytes, and flow conditions. Corrosion can be detrimental if left untreated. For example, untreated corrosion can result in an asset becoming inefficient, unreliable, and in some cases, unsafe. A common solution is to use corrosion inhibitor, which can form a protective barrier against corrosive attack.

SUMMARY

Certain aspects of the subject matter described can be implemented as a method for determining corrosion inhibitor residual concentration of a hydrocarbon sample. The hydrocarbon sample is mixed with a standard solution to form a first mixture. The standard solution includes a corrosion inhibitor in a known concentration. The first mixture is mixed with an aqueous saline solution to form a second mixture. The aqueous saline solution includes about 1% salt concentration or greater. The second mixture is agitated for about 1 hour or longer and at a temperature of about 50 degrees Celsius (° C.) or greater. After agitation, a hydrocarbon phase and an aqueous phase of the second mixture are allowed to separate. A portion of the aqueous phase is obtained. The portion of the aqueous phase is analyzed to determine a corrosion inhibitor residual concentration of the hydrocarbon sample.

This, and other aspects, can include one or more of the following features.

In some implementations, the known concentration of the corrosion inhibitor in the standard solution is in a range of from about 100 parts per million (ppm) to about 10,000 ppm. In some implementations, a concentration of the corrosion inhibitor in the first mixture is in a range of from 50 ppm to about 150 ppm. In some implementations, the aqueous saline solution includes about 5% salt concentration or less. In some implementations, a ratio of the first mixture to the aqueous saline solution in the second mixture is about 1:1. In some implementations, the hydrocarbon sample has a water content of up to 5 volume percent (vol. %).

In some implementations, the second mixture is agitated for about 3 hours or less. In some implementations, the second mixture is agitated at a temperature of about 90° C. or less. In some implementations, allowing the hydrocarbon phase and the aqueous phase of the second mixture to separate includes allowing the second mixture to sit and cool for about 1 day.

In some implementations, analyzing the portion of the aqueous phase includes performing reversed-phase chromatography on the portion of the aqueous phase with a mobile phase comprising methanol and a phosphate buffer. In some implementations, a ratio of methanol to phosphate buffer in the mobile phase is about 1:1. In some implementations, the mobile phase has a pH of about 2.5.

Certain aspects of the subject matter described can be implemented as a method. A hydrocarbon sample is obtained. The hydrocarbon sample is divided into test samples. A standard solution is added to each test sample. The standard solution includes a corrosion inhibitor in a known concentration. A first aqueous saline solution having a first salt concentration is added to a first portion of test samples. A second aqueous saline solution having a second salt concentration is added to a second portion of test samples. A third aqueous saline solution having a third salt concentration is added to a third portion of test samples. The first, second, and third salt concentrations are different from each other. An extraction is performed on each of the test samples. Performing the extraction includes agitating a fourth portion of test samples for a first time duration, a fifth portion of test samples for a second time duration, and a sixth portion of test samples for a third time duration. The first, second, and third time durations are different from each other. Performing the extraction includes maintaining a seventh portion of test samples at a first temperature, an eighth portion of test samples at a second temperature, and a ninth portion of test samples at a third temperature. The first, second, and third temperatures are different from each other. After performing the extraction on each of the test samples, a hydrocarbon phase and an aqueous phase of each of the test samples are allowed to separate. A portion of the aqueous phase of each of the test samples are obtained. The portion of the aqueous phase of each of the test samples are analyzed to determine a corrosion inhibitor residual concentration of the hydrocarbon sample.

This, and other aspects, can include one or more of the following features.

In some implementations, the known concentration of the corrosion inhibitor in the standard solution is in a range of from about 100 ppm to about 10,000 ppm. In some implementations, a concentration of the corrosion inhibitor in the each of the test samples after addition of the standard solution is in a range of from 50 ppm to about 150 ppm. In some implementations, the first, second, and third salt concentrations are in a range of from about 1% to about 5%. In some implementations, a ratio of the hydrocarbon sample to the first aqueous saline solution in each of the first portion of test samples is about 1:1. In some implementations, a ratio of the hydrocarbon sample to the second aqueous saline solution in each of the second portion of test samples is about 1:1. In some implementations, a ratio of the hydrocarbon sample to the third aqueous saline solution in each of the third portion of test samples is about 1:1.

In some implementations, the first, second, and third time durations are in a range of from about 1 hour to about 3 hours. In some implementations, the first, second, and third temperatures are in a range of from about 50° C. to about 90° C. In some implementations, allowing the hydrocarbon phase and the aqueous phase of each of the test samples to separate includes allowing each of the test samples to sit and cool for about 1 day.

In some implementations, analyzing the portion of the aqueous phase of each of the test samples comprises performing reversed-phase chromatography on the portion of the aqueous phase of each of the test samples with a mobile phase comprising methanol and a phosphate buffer. In some implementations, a ratio of methanol to phosphate buffer in the mobile phase is about 1:1. In some implementations, the mobile phase has a pH of about 2.5.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes monitoring residual corrosion inhibitor content in hydrocarbon-containing fluids. Without effective corrosion inhibitor monitoring, it can be difficult to determine whether an optimum amount of inhibitor is being used in a hydrocarbon-handling system. Using too much inhibitor can be costly (the excess inhibitor provides no further benefit) and can cause an upset to the system. Using too little inhibitor can leave equipment and piping at risk of corrosive attack. Determining the optimum amount of inhibitor can be beneficial, by resulting in a reduction in costs (associated with using excess inhibitor) as well as a reduction in the amount of inhibitor (which can be toxic) being discharged to the environment after use.

The subject matter described in this disclosure can be implemented in particular implementations, so as to realize one or more of the following advantages. The methods described can be implemented to determine inhibitor residual concentration in dry crude oil that includes negligible amounts of an aqueous phase. The methods described can be implemented to determine the optimum amount of corrosion inhibitor to include at the inlet of a gas oil processing plant. The methods described can be implemented to determine optimum temperature, time, and water salinity for a corrosion inhibitor extraction process to be able to accurately measure the corrosion inhibitor concentration. The methods described can be implemented to optimize chemical treatment in a gas oil processing plant and can reduce operating costs, maintain process integrity, and extend overall working life of the plant.

Figure 1:
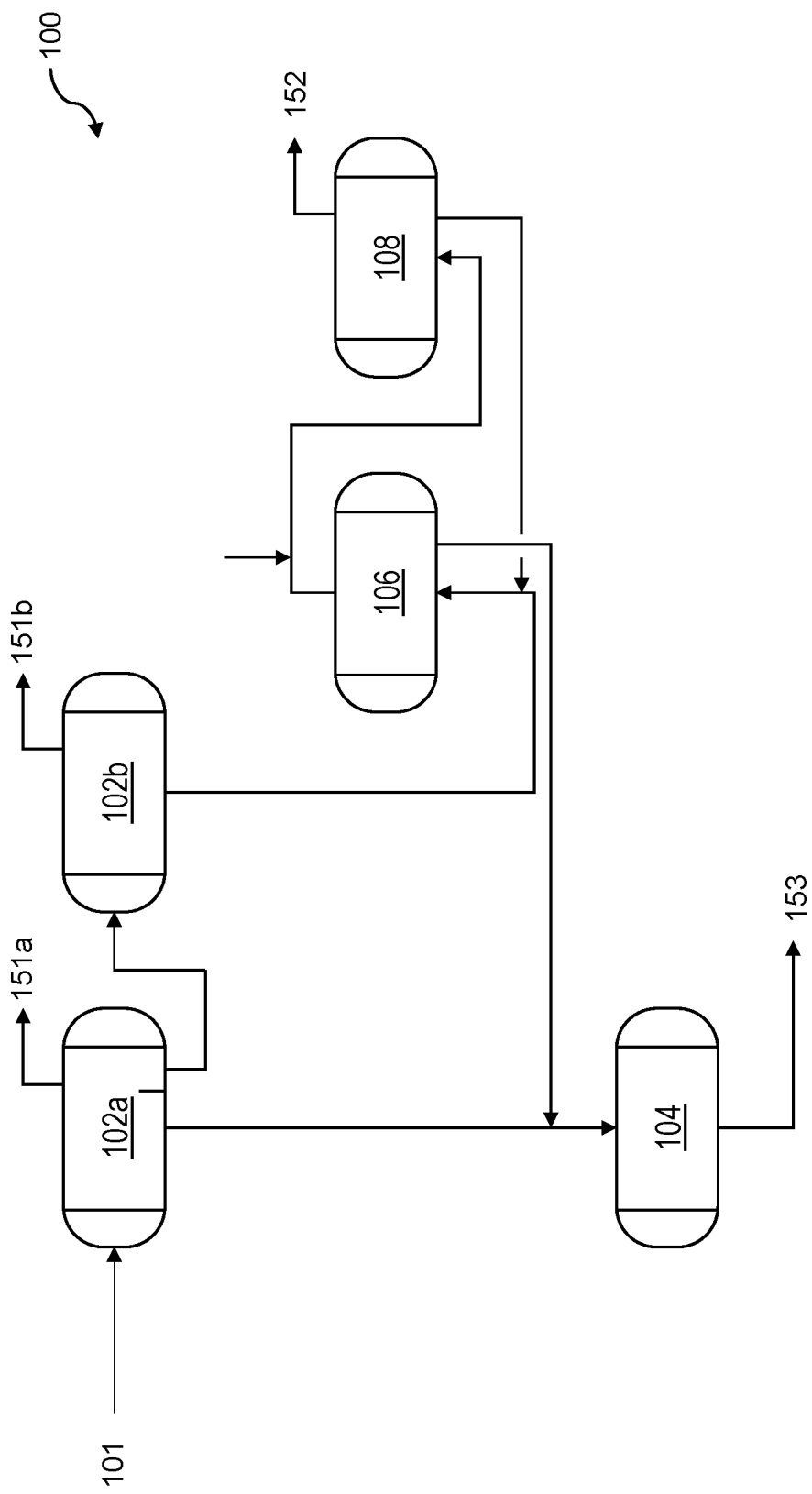
FIG. 1 is a schematic diagram of an example hydrocarbon processing system.

FIG. 1 depicts a gas oil processing plant 150 that separates production fluid 101 (for example, crude oil) from a well into constituent vapor (gas 151) and liquid (oil 152 and produced water 153) components. The production fluid 101 may include corrosion inhibitor. The production fluid 101 flows to a high pressure production trap 102a, where the production fluid 101 is separated into a high pressure gas 151a, an oily phase, and an aqueous phase. The aqueous phase (which may include some oil) from the high pressure production trap 102a flows to a water-oil separator 104. The oily phase (which may include some water) from the high pressure production trap 102a flows to a low pressure production trap 102b. The low pressure production trap 102b operates at a decreased pressure relative to the high pressure production trap 102a. Volatile components flash from the oily phase at the decreased pressure, and a low pressure gas 151b is separated from the oily phase in the low pressure production trap 102b. The oily phase (which may include some water) from the low pressure production trap 102b flows to a dehydrator 106. The dehydrator 106 promotes separation of oily and aqueous phases. The aqueous phase from the dehydrator 106 flows to the water-oil separator 104. In some implementations, the aqueous phase from the dehydrator 106 combines with the aqueous phase from the high pressure production trap 102a before they flow together to the water-oil separator 104. The water-oil separator 104 promotes separation of oily and aqueous phases. The oily phase can form on top of the aqueous phase within the water-oil separator 104 and be skimmed and removed from the water-oil separator 104. The aqueous phase from the water-oil separator 104 is produced water 153 and can be injected back into the Earth, for example, via an injection well.

The oily phase (which may include some water) from the dehydrator 106 flows to a desalter 108. In some implementations, wash water combines with the oily phase from the dehydrator 106 before they flow together to the desalter 108. The desalter 108 also promotes separation of oily and aqueous phases. Dry crude oil 152 is separated from the aqueous phase in the desalter 108. The aqueous phase from the desalter 108 can be recycled to the dehydrator 106. In some implementations, the aqueous phase from the desalter 108 combines with the oily phase from the low pressure production trap 102b before they flow together to the dehydrator 106.

The gas oil processing plant 150 also includes typical processing equipment (not shown), such as mixers and/or mixing valves, pumps, control valves, storage tanks, heat exchangers, and compressors. The gas 151a, 151b from the gas oil processing plant 150 can be burned as fuel or further processed, for example, at a gas processing plant. The stabilized crude oil 152 (also referred as dry crude oil) from the gas oil processing plant 150 can be further processed, for example, at a crude oil refinery. In some implementations, the dry crude oil 152 is free of water (that is, a water content of 0%). In some implementations, the dry crude oil 152 is substantially free of water. For example, the dry crude oil 152 has a water content of up to 5 volume % (vol. %), less than 5 vol. %, less than 4 vol. %, less than 3 vol. %, less than 2 vol. %, less than 1 vol. %, less than 0.5 vol. %, or less than 0.1 vol. %. Although shown in FIG. 1 as including single instances of the equipment (102a, 102b, 104, 106, 108), the plant 150 can include additional implementations of one or more of the shown equipment in parallel configurations, serial configurations, or a combination of both.

Figure 2A:
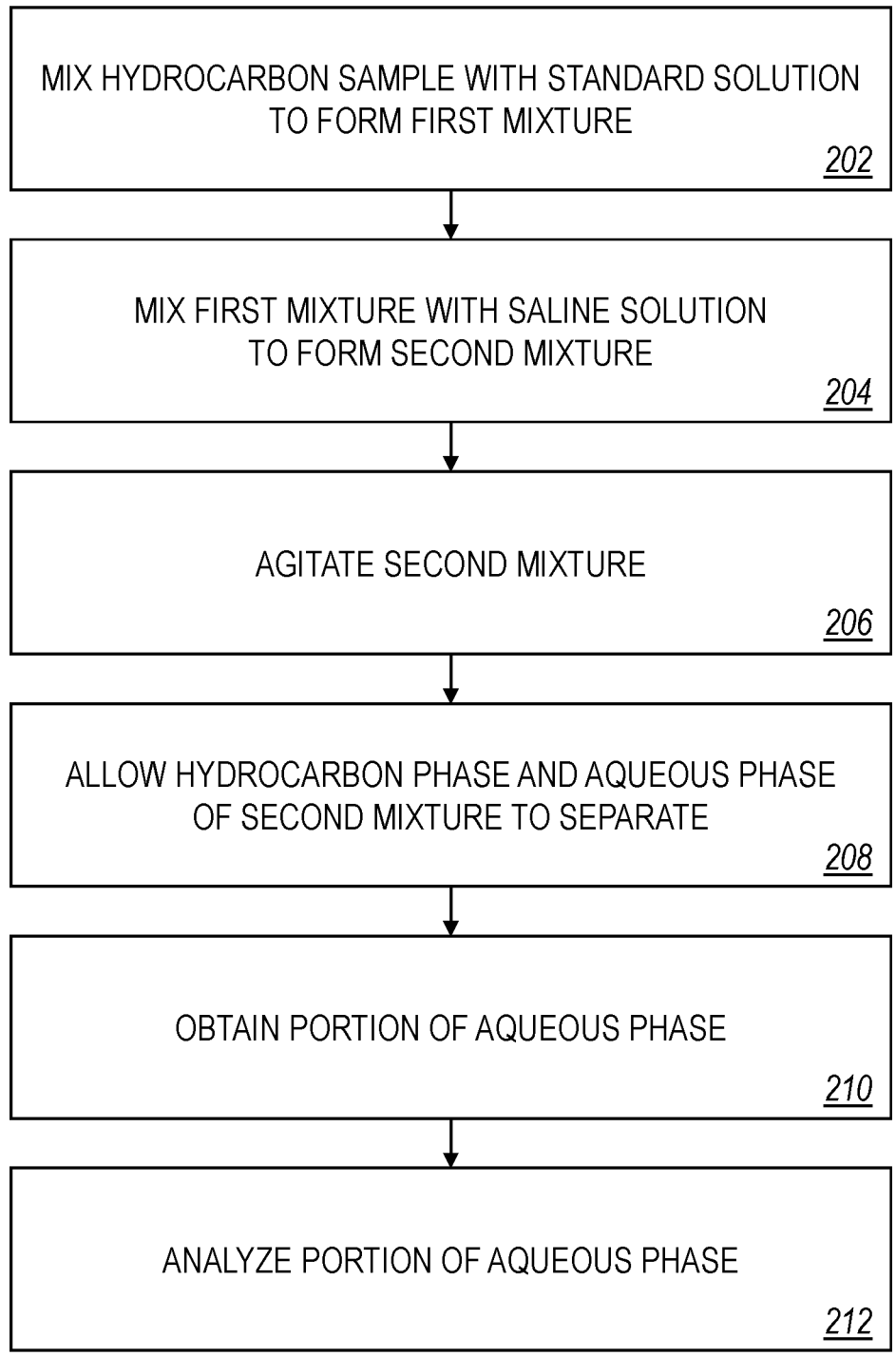
FIG. 2A is a flow chart of an example method for determining residual corrosion inhibitor content in hydrocarbon samples.

FIG. 2A is a flow chart of a method 200A for determining residual corrosion inhibitor content in a hydrocarbon sample. The hydrocarbon sample can be, for example, a sample of the dry crude oil 152. At step 202, the hydrocarbon sample is mixed with a standard solution to form a first mixture. The standard solution includes a corrosion inhibitor in a known concentration. In some implementations, a concentration of the corrosion inhibitor in the standard solution is in a range of from about 100 parts per million (ppm) to about 10,000 ppm. In some implementations, a ratio of the hydrocarbon sample to the standard solution in the first mixture is in a range of from about 50:1 to about 100:1. In some implementations, a concentration of the corrosion inhibitor in the first mixture is in a range of from 50 ppm to about 150 ppm.

At step 204, the first mixture is mixed with an aqueous saline solution to form a second mixture. In some implementations, the aqueous saline solution includes about 1% salt concentration (by mass) or greater. In some implementations, the aqueous saline solution includes about 5% salt concentration or less. In some implementations, the aqueous saline solution has a salt concentration in a range of from about 1% to about 5%. In some implementations, a ratio of the first mixture to the aqueous saline solution in the second mixture is in a range of from about 1:2 to about 2:1. For example, the ratio of the first mixture to the aqueous saline solution in the second mixture is about 1:1.

At step 206, the second mixture is agitated for about 1 hour or longer and at a temperature of about 50 degrees Celsius (° C.) or greater. In some implementations, the second mixture is agitated for about 3 hours or less at step 206. In some implementations, the second mixture is agitated for a time duration in a range of from about 1 hour to about 3 hours. In some implementations, the second mixture is agitated at a temperature of about 90° C. or less at step 206. In some implementations, the second mixture is agitated at a temperature in a range of from about 50° C. to about 90° C. at step 206.

After agitation at step 206, a hydrocarbon phase and an aqueous phase of the second mixture are allowed to separate at step 208. In some implementations, allowing the hydrocarbon phase and the aqueous phase of the second mixture to separate at step 208 includes allowing the second mixture to sit and cool for about 1 day.

At step 210, a portion of the aqueous phase is obtained. At step 212, the portion of the aqueous phase is analyzed to determine a corrosion inhibitor residual concentration of the hydrocarbon sample. In some implementations, analyzing the portion of the aqueous phase at step 212 includes performing reversed-phase chromatography on the portion of the aqueous phase with a mobile phase. The mobile phase is used to elute analytes (such as corrosion inhibitor) from a reversed-phase column. In some implementations, the reversed-phase column has a length of about 25 centimeters. In some implementations, the mobile phase includes methanol and a phosphate buffer. In some implementations, a ratio of methanol to phosphate buffer in the mobile phase is about 1:1. The pH of the mobile phase can affect retention of an analyte and selectivity of certain analytes. In some implementations, the mobile phase has a pH of about 2.5. In some implementations, the detector used to analyze the portion of the aqueous phase at step 212 employs analytical wavelengths of about 300 nanometers (nm) for excitation and about 380 nm for emission.

Figure 2B:
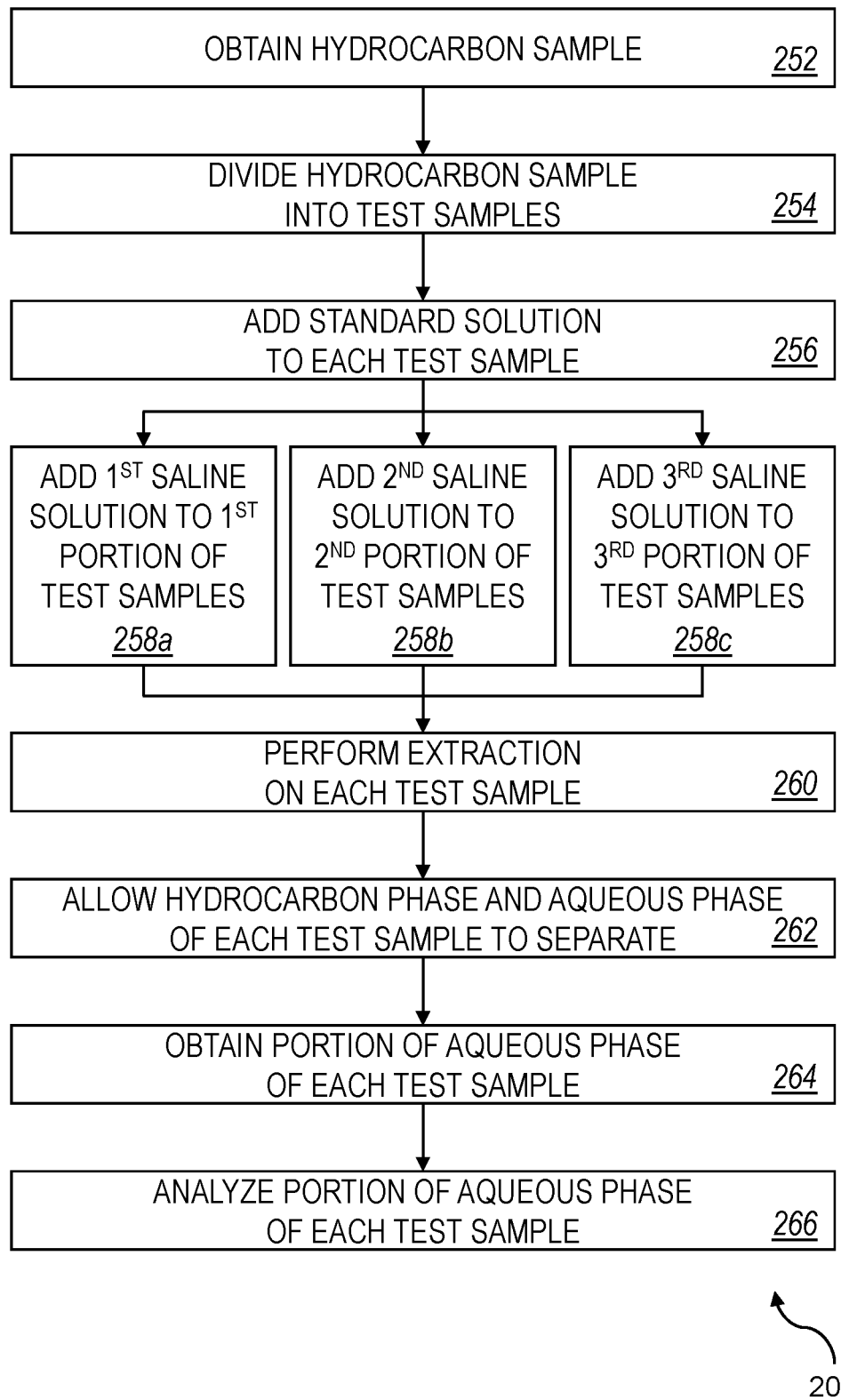
FIG. 2B is a flow chart of an example method for determining residual corrosion inhibitor content in hydrocarbon samples.

FIG. 2B is a flow chart of a method 200B for determining residual corrosion inhibitor content in hydrocarbon samples. The hydrocarbon sample can be, for example, a sample of the dry crude oil 152. At step 252, the hydrocarbon sample is obtained. At step 254, the hydrocarbon sample is divided into test samples.

At step 256, a standard solution including a corrosion inhibitor in a known concentration is added to each test sample. In some implementations, a concentration of the corrosion inhibitor in the standard solution is in a range of from about 100 ppm to about 10,000 ppm. In some implementations, a ratio of the hydrocarbon sample to the standard solution in each of the test samples is in a range of from about 50:1 to about 100:1. In some implementations, a concentration of the corrosion inhibitor in the each of the test samples after addition of the standard solution is in a range of from 50 ppm to about 150 ppm.

At step 258a, a first aqueous saline solution having a first salt concentration is added to a first portion of the test samples. At step 258b, a second aqueous saline solution having a second salt concentration is added to a second portion of the test samples. At step 258c, a third aqueous saline solution having a third salt concentration is added to a third portion of the test samples. The first, second, and third salt concentrations are different from each other. In some implementations, the first, second, and third salt concentrations are in a range of from about 1% to about 5%. In some implementations, a ratio of the hydrocarbon sample to the first aqueous saline solution in each of the first portion of test samples is in a range of from about 1:2 to about 2:1. For example, the ratio of the hydrocarbon sample to the first aqueous saline solution in each of the first portion of test samples is about 1:1. In some implementations, a ratio of the hydrocarbon sample to the second aqueous saline solution in each of the second portion of test samples is in a range of from about 1:2 to about 2:1. For example, the ratio of the hydrocarbon sample to the second aqueous saline solution in each of the second portion of test samples is about 1:1. In some implementations, a ratio of the hydrocarbon sample to the third aqueous saline solution in each of the third portion of test samples is in a range of from about 1:2 to about 2:1. For example, the ratio of the hydrocarbon sample to the third aqueous saline solution in each of the third portion of test samples is about 1:1.

At step 260, an extraction is performed on each of the test samples. Performing the extraction at step 260 includes agitating a fourth portion of test samples for a first time duration, agitating a fifth portion of test samples for a second time duration, and agitating a sixth portion of test samples for a third time duration. The first, second, and third time durations are different from each other. In some implementations, the first, second, and third time durations are in a range of from about 1 hour to about 3 hours. Performing the extraction at step 260 includes maintaining a seventh portion of test samples at a first temperature, maintaining an eight portion of test samples at a second temperature, and maintaining a ninth portion of test samples at a third temperature. The first, second, and third temperatures are different from each other. In some implementations, the first, second, and third temperatures are in a range of from about 50° C. to about 90° C.

After performing the extraction on each of the test samples at step 260, a hydrocarbon phase and an aqueous phase of each of the test samples are allowed to separate at step 262. In some implementations, allowing the hydrocarbon phase and the aqueous phase of each of the test samples to separate at step 262 includes allowing each of the test samples to sit and cool for about 1 day.

At step 264, a portion of the aqueous phase of each of the test samples is obtained. At step 266, the portion of the aqueous phase of each of the test samples is analyzed to determine a corrosion inhibitor residual concentration of the hydrocarbon sample. In some implementations, analyzing the portion of the aqueous phase of each of the test samples at step 266 includes performing reversed-phase chromatography on the portion of the aqueous phase of each of the test samples with a mobile phase. In some implementations, the mobile phase includes methanol and a phosphate buffer. In some implementations, a ratio of methanol to phosphate buffer in the mobile phase is about 1:1. In some implementations, the mobile phase has a pH of about 2.5.

In some implementations, the first, second, and third portions of test samples are mutually exclusive portions. For example, test sample(s) of the first portion are not part of the second and third portions. In some implementations, the fourth, fifth, and sixth portions of test samples are mutually exclusive portions. For example, test sample(s) of the fourth portion are not part of the fifth and sixth portions. In some implementations, the seventh, eighth, and ninth portions of test samples are mutually exclusive portions. For example, test sample(s) of the seventh portion are not part of the eighth and ninth portions. The first, second, and third portions of test samples can be considered "Split A". The fourth, fifth, and sixth portions of test samples can be considered "Split B". The seventh, eighth, and ninth portions of test samples can be considered "Split C". Portions of test samples of "Split A" and portions of test samples of "Split B" are not necessarily mutually exclusive. For example, test sample(s) of the first portion can also be a part of the fourth portion. Portions of test samples of "Split A" and portions of test samples of "Split C" are not necessarily mutually exclusive. For example, test sample(s) of the second portion can also be a part of the seventh portion. Portions of test samples of "Split B" and portions of test samples of "Split C" are not necessarily mutually exclusive. For example, test sample(s) of the fifth portion can also be a part of the eighth portion.

Example

Treated crude oil samples were collected from different facilities that have similar grade of crude oil and mixed together in 20 liter Nalgene container. A standard solution of Cortron AR-505 (corrosion inhibitor) was prepared by diluting 0.45 grams of the neat chemical with 50 mL of methanol to make 9000 ppm solution. In 1 liter glass bottle, 300 milliliter (mL) of treated crude oil was spiked with corrosion inhibitor solution to make the final concentration 100 ppm. This spiking was repeated with all crude oil samples. Saline water was then prepared by dissolving sodium chloride in de-ionized water to make different salinities 1%, 3%, and 5% that was utilized for all extractions.

For extraction, 300 mL of saline water was added to the 1 liter glass bottles that contains the spiked crude oil and placed inside the oil bath on the digital hot plate stirrer. Extractions were carried out at three different temperatures 50° C., 70° C., and 90° C. for three different extraction times: 60 min, 120 min, and 180 min. After each extraction, the mixture was cooled and let stand for 1 day or until the oil and water mixture separated completely. Once the mixture separated, an aliquot was collected from the water layer using a pipette and then transferred to a 2 mL vial for liquid chromatography (LC) analysis.

LC reversed-phase system with an Agilent Zorbax Eclipse XDB C18 column and fluorescence detector was utilized for the analysis. The mobile phase used has a ratio of 1:1 methanol to phosphate buffer at pH of 2.5. Analysis mode with an isocratic with a column temperature of 40° C. and a flowrate of 1 mL/min. Each instrumental analysis run lasts for 15 minutes and the targeted analyte was eluting at 10.5 min. The calibration of the LC system was carried out by standards that were prepared from the 9000 ppm stock solution and diluted to result in 1 ppm, 10 ppm, 20 ppm, 50 ppm, 100 ppm, and 200 ppm standards.

Figure 3A:
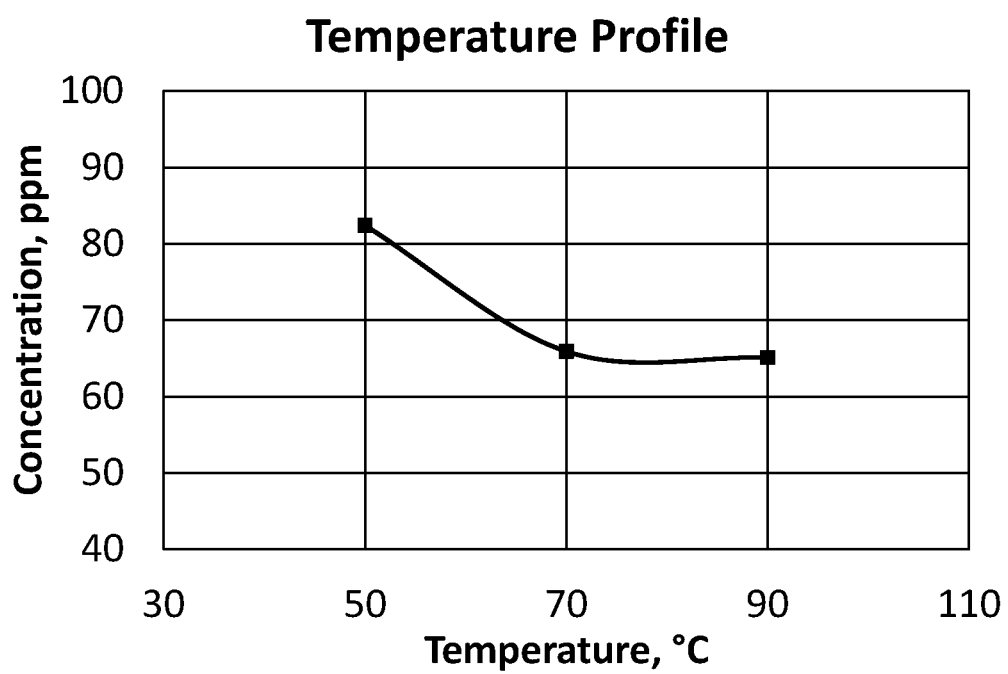
FIG. 3A is a plot showing a temperature profile of a corrosion inhibitor extraction process.

FIG. 3A is a plot showing a temperature profile of the corrosion inhibitor extraction process. The extraction temperatures studied were 50° C., 70° C., and 90° C. Extraction time and salinity were constant at 180 minutes and 1%, respectively. Increasing the extraction temperature to be greater than 50° C. did not improve the extraction process.

Figure 3B:
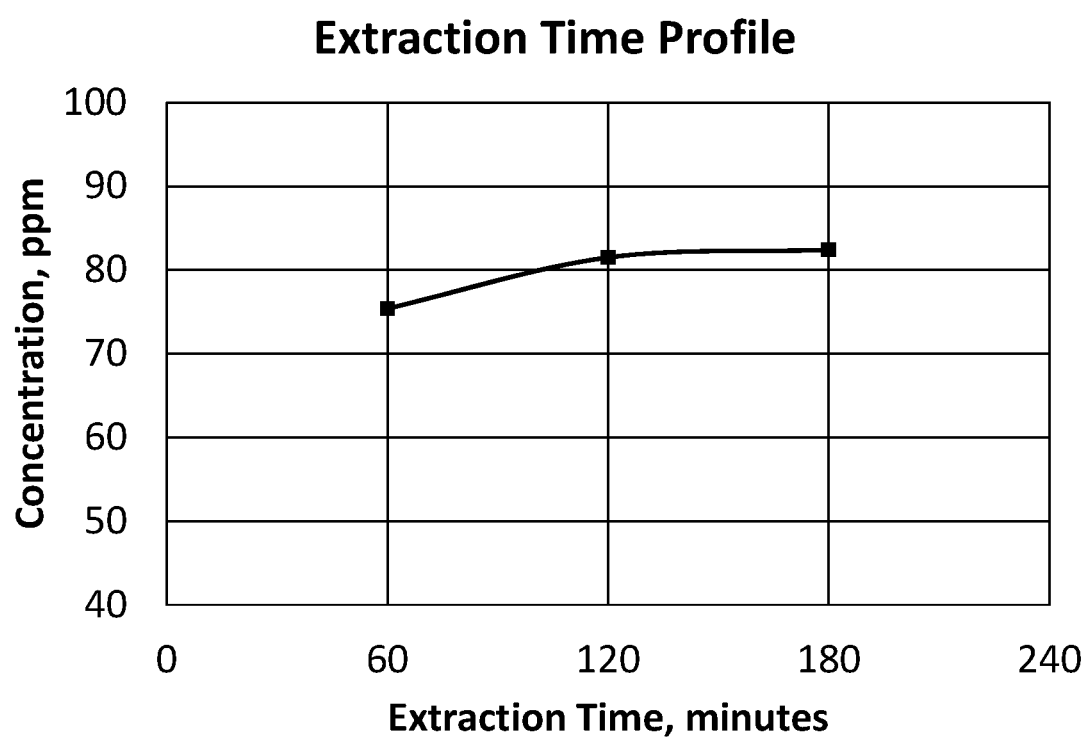
FIG. 3B is a plot showing a time profile of a corrosion inhibitor extraction process.

FIG. 3B is a plot showing a time profile of the corrosion inhibitor extraction process. The extraction times studied were 60 minutes, 120 minutes, and 180 minutes. Extraction temperature and salinity were constant at 50° C. and 1%, respectively. Increasing the extraction time to be longer than 60 minutes improved the extraction process by allowing sufficient time to separate phases. The benefits of increasing extraction time appears to plateau, so extending the extraction time much further past 180 minutes may not be necessary.

Figure 3C:
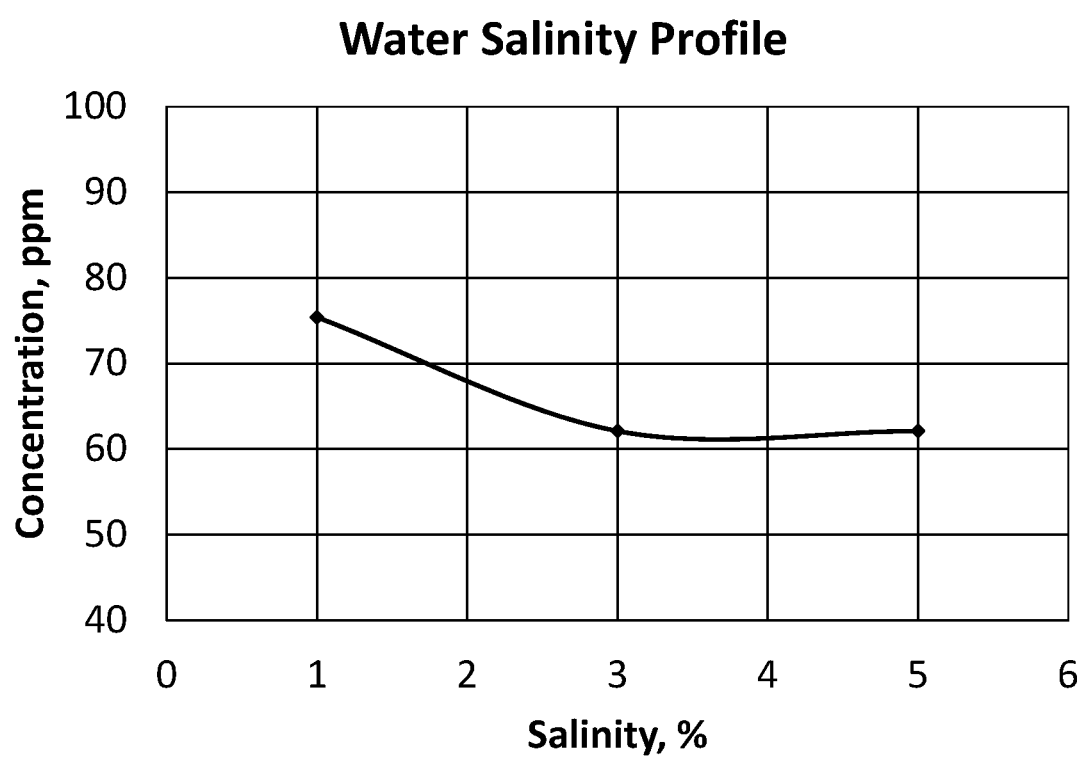
FIG. 3C is a plot showing a water salinity profile of a corrosion inhibitor extraction process.

FIG. 3C is a plot showing a water salinity profile of the corrosion inhibitor extraction process. The extraction water salinities studied were 1%, 3%, and 5%. Extraction time and temperature were constant at 60 minutes and 50° C., respectively. Increasing the water salinity to be greater than 1% did not improve the extraction process. When ions and organic species exist together with water, water can tend to solvate the ions rather than the organic species (such as the corrosion inhibitor), even if the organic species are soluble in water.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

As used in this disclosure, the term "analyte" refers to a component that is of interest in an analytical procedure. For example, an analyte is a substance that is being identified and measured in a chemical analysis.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method for determining corrosion inhibitor residual concentration of dry crude oil, the method comprising:
   mixing the dry crude oil with a standard solution to form a first mixture, the standard solution comprising a corrosion inhibitor in a known concentration;
   mixing the first mixture with an aqueous saline solution to form a second mixture, the aqueous saline solution comprising about 1% salt concentration or greater;
   agitating the second mixture for about 1 hour or longer and at a temperature of about 50 degrees Celsius (° C.) or greater;
   after agitation, allowing a hydrocarbon phase and an aqueous phase of the second mixture to separate;
   obtaining a portion of the aqueous phase; and
   analyzing the portion of the aqueous phase with reversed phase liquid chromatography using a mobile phase having a mixture of methanol to phosphate buffer at a 1:1 ratio and a pH of about 2.5 to determine a corrosion inhibitor residual concentration of the dry crude oil.

2. The method of claim 1, wherein the known concentration of the corrosion inhibitor in the standard solution is in a range of from about 100 parts per million (ppm) to about 10,000 ppm.

3. The method of claim 1, wherein a concentration of the corrosion inhibitor in the first mixture is in a range of from 50 ppm to about 150 ppm.

4. The method of claim 1, wherein the aqueous saline solution comprises about 5% salt concentration or less.

5. The method of claim 1, wherein a ratio of the first mixture to the aqueous saline solution in the second mixture is about 1:1.

6. The method of claim 1, wherein the second mixture is agitated for about 3 hours or less.

7. The method of claim 1, wherein the second mixture is agitated at a temperature of about 90° C. or less.

8. The method of claim 1, allowing the hydrocarbon phase and the aqueous phase of the second mixture to separate comprises allowing the second mixture to sit and cool for about 1 day.

9. The method of claim 1, wherein the dry crude oil has a water content of less than 0.5 volume percent (vol. %).

* * * * *